United States Patent
Ravikumar

(10) Patent No.: US 7,820,810 B2
(45) Date of Patent: Oct. 26, 2010

(54) PROCESS FOR THE SYNTHESIS OF 2'-O-SUBSTITUTED PURINE NULCEOSIDES

(75) Inventor: Vasulinga Ravikumar, Carlsbad, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 393 days.

(21) Appl. No.: 12/051,610

(22) Filed: Mar. 19, 2008

(65) Prior Publication Data

US 2008/0234475 A1 Sep. 25, 2008

Related U.S. Application Data

(60) Provisional application No. 60/895,650, filed on Mar. 19, 2007.

(51) Int. Cl.
*C07H 21/00* (2006.01)
(52) U.S. Cl. .................... 536/25.3; 536/18.5; 536/18.6; 536/25.31
(58) Field of Classification Search ........................ None
See application file for complete search history.

(56) References Cited

U.S. PATENT DOCUMENTS

| | | | |
|---|---|---|---|
| 5,466,786 | A | 11/1995 | Buhr et al. |
| 5,750,673 | A | 5/1998 | Martin |
| 5,760,202 | A | 6/1998 | Cook et al. |
| 6,166,367 | A | 12/2000 | Cook et al. |
| 6,222,025 | B1 | 4/2001 | Cook et al. |
| 6,642,367 | B2 | 11/2003 | Cook et al. |

FOREIGN PATENT DOCUMENTS

| | | |
|---|---|---|
| DE | 4110085 | 10/1992 |
| EP | 0260032 | 3/1988 |
| EP | 0339842 | 11/1989 |
| EP | 0614907 | 9/1994 |
| EP | 0629633 | 12/1994 |
| EP | 0714907 | 6/1996 |
| JP | 89-85456 | 4/1989 |
| JP | 2-264792 | 10/1990 |
| JP | 6-507883 | 9/1994 |
| JP | 6-345791 | 12/1994 |
| JP | 7-002889 | 1/1995 |
| JP | 7-300493 | 11/1995 |
| JP | 8-208686 | 8/1996 |
| JP | 9-508134 | 8/1997 |
| WO | WO 95/35102 | 12/1995 |
| WO | WO 96/27606 | 9/1996 |

OTHER PUBLICATIONS

Agrawal (Ed.), "Protocols for Oligonucleotides and Analogs" Humana Press, Totowa, NJ, 1993.
Blackburn et al., "Nucleic Acids in Chemistry and Biology" Chapter 3, p. 98, IRL Press, New York, 1990.
Chavis et al., "Synthesis of 2',3'-Differentiated Ribonucleosides via Glycosylation Reactions with 2-O-Me or 2-O-TBDMS Ribofuranose Derivatives. 1. Pyrimidine Series" J. Org. Chem. (1982) 47:202-206.
Cotten et al., "2-O-methyl, 2'-O-ethyl oligoribonucleotides and phosphorothioate oligodeoxyribonucleotides as inhibitors of the in vitro U7 snRNP-dependent mRNA processing event" Nucl. Acids Res. (1991) 19(10):2629-2635.
Divakar et al., "Reaction Between 2,2'-Anhydro-1-B-D-arabinofuranosyluracil and Thiolate Ions" J. Chem. Soc. Perkin Trans. (1982) 1625-1628.
Edmonds et al., "Structural Characterization of Four Ribose-methylated Nucleosides from the Transfer RNA of Extremely Thermophilic Archaebacteria" J. Chem. Soc., Chem. Commun. (1987) 909-910.
Fraser et al., "Synthesis & conformational properties of 2'-deoxy-2'-methylthio-pyrimidine & -purine nucleosides: potential antisense applications" J. of Heterocyclic Chem. (1993) 30:1277-1287.
Gotfredsen et al., "Novel Oligodeoxynucleotide Analogues Containing A 2'-O-Methylarabinonucleoside" Tetra. Letts. (1994) 35(37):6941-6944.
Greene et al., "Protective Groups in Organic Synthesis" John Wiley & Sons, New York, 2nd edition, 1991, Chap. 2,6,7.
Guinosso et al., "Synthesis and Biophysical and Biological Evaluation of 2'-Modified Antisense Oligonucleotides" Nucleosides & Nucleotides (1991) 10(1-3)259-262.
Haralambidis et al., "Preparation of Base-Modified Nucleosides Suitable for Non-Radioactive Label Attachment and Their Incorporation Into Synthetic Oligodeoxyribonucleotides" Nucleic Acids Research (1987) 15(12):4857-4875.
Herdewijn et al., "Synthesis and Anti-HIV Activity of Different Sugar-Modified Pyrimidine and Purine Nucleosides" J. Med. Chem. (1988) 31:2040-2048.
Holy, "Nucleic acid components and their analogues, CLV" Coll. Czech. Chem. Commun. (1973) 38:423-427.
Ikehara et al., "Studies of Nucleosides and Nucleotides. LXXII. Purine Cyclonucleosides.33. A New Method for the Synthesis of 8,2'-S-Cyclonucleosides" J. Carbohydrates, Nucleosides, Nucleotides (1977) 4(6):409-413.
Inoue et al., "Synthesis and properties of novel nucleic acid probes" Nucl. Acids Res. (1985) 165-168.
Inoue et al., "Synthesis and hybridization studies on two complementary nona(2'-O-methyl)ribonucleotides" Nucl. Acids Res. (1987) 15(15):6131-6148.
Iribarren et al., "2'-O-Alkyl oligoribonucleotides as antisense probes" PNAS (1990) 87:7747-7751.
Kaneko et al., "Synthesis and Properties of 8,2'-Cyclothioguanosine and Related Compounds" Chem. Pharm. Bull. (1972) 20(3):635-637.
Keller et al., "A General Method for the Synthesis of 2'-O-Modified Ribonucleosides" Helv. Chim. Acta (1993) 76:884-892.

(Continued)

Primary Examiner—Patrick T Lewis

(57) ABSTRACT

The present invention provides an improved process for the synthesis of 2'-O-substituted purine nucleosides. The process includes anhydro or thioanhydro ring opening of a selected 8,2'-cyclopurine nucleoside with a weak nucleophile in the presence of a Lewis acid ester, followed by reduction to afford the desired 2'-O-substituted purine nucleoside.

40 Claims, No Drawings

OTHER PUBLICATIONS

Kois et al., "Synthesis and Some Properties of Modified Oligonucleotides. 2. Oligonucleotides Containing 2'-Deoxy-2'-Fluoro-B-D-Arabinofuranosyl Pyrimidine Nucleosides" Nucleosides & Nucleotides (1993) 12(10):1093-1109.

Kroschwitz ed., "Concise Encyclopedia of Polymer Science and Engineering" pp. 858-859, John Wiley & Sons, New York, 1990.

Kusmierek et al., "Alkylation of Cytidine-5'-Phosphate: Mechanisms of Alkylation, Influence of O'-Alkylation of Susceptibility of Pyrimidine nucleotides to Some Nucleolytic Enzymes, and Synthesis of 2'-O-Alkyl Polynucleotides" Acta. Biochimica Polonica (1973) 20(4):365-381.

Kusmierek et al., "Preparation and stability of the helical form of poly 2'-O-ethyluridylic acid" Biochem. Biophys. Res. Commun. (1973) 53(2): 406-412.

Kusmierek et al., "Preparation of O'-Alkyl Derivatives of Cytosine and Uracil Nucleosides" Biochem. (1973) 12(2): 194-200.

Lamond et al., "Antisense oligonucleotides made of 2'-O-alkyl RNA: their properties & applications in RNA biochemistry" FEBS Letts (1993) 325(1,2): 123-127.

Liu et al., "Deacetylation of 2'-O-Ts-3',5'-di-O-acetylpurine nucleosides via a free radical reaction" J. Chem. Research (2003) 706-707.

Manoharan, "Designer antisense oligonucleotides: conjugation chemistry and functionality placement" 310-312 in "Antisense Research and Applications" Crooke and Lebleu (Eds.), CRC Press, Boca Raton, 1993.

March, "Advanced organic chemistry-reactions, mechanisms, and structure" John Wiley & Sons, New York, 1985, 227-229.

Martin, "A New Access to 2'-O-Alkylated Ribonucleosides and Properties of 2'-O-Alkylated Oligoribonucleotides" Helv. Chim. Acta (1995) 78:486-504.

McGee et al., "Reaction of anhydronucleosides with magnesium alkoxides: regiospecific synthesis of 2'-O-Alkylpyrimidine nucleosides" Nucleosides & Nucleotides (1996) 15(11&12): 1797-1803.

Ogilvie et al., "Synthesis of 8,2'-Thioanhydroguanosine" Canadian Journal of Chemistry (1972) 50:1100-1104.

Ogilvie et al., "A General Synthesis of 8,2'-Thioanhydropurine Nucleosides" Canadian Journal of Chemistry (1972) 50:2249-2253.

Ogilvie et al., "Synthesis of 8,2'-Cyclopurinenucleosides" Canadian Journal of Chemistry (1972) 9:1179-1180.

Ransford et al., "2-O-Ethyl Pyrimidine Nucleosides (1)" J. Carbohydrates, Nucleosides, Nucleotides (1974) 1(3): 275-278.

Robins et al., "Nucleic Acid Related Compounds. 1. Methylation and Transformation of 4-Methoxy-2-pyrimidinone 1-B-D-Ribofuranoside into 2'-O-Methyl Nucleoside Components of Ribonucleic Acid, Their Analogs, and Derivatives" Biochem. (1971) 10(19) 3591-3597.

Ross et al., "A Novel and Economical Synthesis of 2'-O-Alkyl-Uridines" Nucleosides & Nucleotides (1997) 16(7-9): 1641-1643.

Ross et al., "Kilo-Scale Synthesis Process for 2'O-(2-Methoxyethyl)-Pyrimidine Derivatives" Nucleosides, Nucleotides, and Nucleic Acids (2005) 24(5-7):815-818.

Sato et al., "Synthesis of 2-Amino-2-deoxy-B-D-arabinofuranosyl Nucleosides" Chem. Pharm. Bull. (1979) 27(9):821-823.

Singer et al., "O2-Alkylcytidine—A New Major Product of Neutral, Aqueous Reaction of Cytidine with Carcinogents" FEBS Lett. (1976) 63(1):85-88.

Townsend, "Chemistry of nucleosides and nucleotides" Plenum Press, NY, 1988, vol. 1., 59-67.

Uhlmann et al., "Antisense oligonucleotides: a new therapeutic principle" Chem. Reviews (1990) 90(4): 543-584.

Vorbruggen et al., "Eine einfache Synthese von 2-Thipyrimidin-nucleosiden" Chem. Ber. (1973) 106:3039-3061.

Wagner et al., "A simple procedure for the preparation of protected 2'-O-methyl or 2'-O-ethyl ribonucleosides-3'-O-phosphoramidites" Nucl. Acids Res. (1991) 19(24):5965-5971.

PROCESS FOR THE SYNTHESIS OF 2'-O-SUBSTITUTED PURINE NULCEOSIDES

RELATED APPLICATIONS

This application claims the benefit under 35 USC 119(e) to U.S. Provisional Application Ser. No. 60/895,650 filed Mar. 19, 2007 which is incorporated herein by reference in its entirety.

FIELD OF THE INVENTION

This present invention provides improved processes for the synthesis of 2'-O-substituted purine nucleosides. More particularly, the present invention provides improved processes for the treatment of a selected 8,2'-cyclopurine nucleoside with a weak base and a Lewis acid ester. The process is expected to be economically advantageous and more efficient relative to processes currently in use and is also expected to be applicable to large scale synthesis.

BACKGROUND OF THE INVENTION

The present invention is directed to new and useful processes for the preparation of 2'-O-substituted purine nucleosides. 2'-O-Substituted purine nucleosides are important compounds used routinely for the synthesis of oligonucleotides and related compounds.

Currently, 2'-O-methoxyethylpurine is prepared from the conversion of a purine into 2,6-diaminopurine riboside using corrosive triflic acid and heating at 150° C. under pressure for several days, followed by the alkylation with methoxyethyl bromide to yield 2,6-diaminopurine riboside, and the conversion back to the desired alkylated 2'-O-methoxyethylpurine using the adenosine deaminase enzyme. However, the alkylation step produces a mixture of various substituted alkylated products including mono-substituted 2'-O-methoxyethyl-2,6-diaminopurine riboside, 3'-O-methoxyethyl-2,6-diaminopurine riboside, and di-substituted 2'-O-3'-O-dimethoxyethyl-2,6-diaminopurine riboside. Furthermore, methoxytheyl bromide is unstable and its $CH_3$—O bond is easily cleaved with traces amount of HBr to generate methyl bromide, which leads to a more reactive electrophile and therefore forming 2'-O-methoxyl-2,6-diaminopurine riboside that is very difficult to be separated. Lastly, the conversion of the already low yielding 2'-O-methoxyl-2,6-diaminopurine riboside requires the use of a relatively expensive adenosine deaminase enzyme to accord the desired 2'-O-methoxyethyl purine in an unattractive overall yield. Therefore, there is a need in the art to discover a more efficient and less expensive method to synthesize 2'-O-methoxyethylpurines.

Oligonucleotides and their analogs have been developed for various uses in molecular biology, including use as probes, primers, linkers, adapters, and gene fragments. Modifications to oligonucleotides used in these procedures include labeling with nonisotopic labels such as fluorescein, biotin, digoxigenin, alkaline phosphatase or other reporter molecules. Modifications also have been made to the ribose phosphate backbone to increase the nuclease stability of the resulting analog. These modifications include use of methyl phosphonates, phosphorothioates, phosphorodithioate linkages, and 2'-O-methyl ribose sugar units. Other modifications have been directed to the modulation of oligonucleotide uptake and cellular distribution. The success of these oligonucleotides for both diagnostic and therapeutic uses has created an ongoing demand for improved oligonucleotide analogs.

Oligonucleotides can be synthesized to have custom properties that are tailored for a desired use. Thus a number of chemical modifications have been introduced into oligonucleotides to increase their usefulness in diagnostics, as research reagents and as therapeutic entities.

SUMMARY OF THE INVENTION

The present invention provides improved processes for the synthesis of 2'-O-substituted purine nucleosides comprising the steps of:

i) providing an 8,2'-cyclopurine nucleoside having an anhydro or thioanhydro linkage in an organic phase; and ii) treating said 8,2'-cyclopurine nucleoside with a reagent that provides an alkoxy radical capable of opening said anhydro linkage thereby providing said 2'-O-substituted purine nucleoside.

In one embodiment, the process further comprises the step of adding triphenylphosphorane or iodine.

In certain embodiments of the invention, said 2'-O-substituted purine nucleoside has formula I:

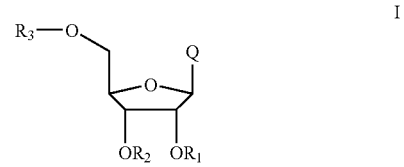

wherein:

Q is an optionally substituted purine;

$R_1$ is substituted or unsubstituted $C_1$-$C_{12}$ alkyl, substituted or unsubstituted $C_2$-$C_{12}$ alkenyl, or substituted or unsubstituted $C_2$-$C_{12}$ alkynyl;

wherein each substituted group independently comprises one or more substituent groups independently selected from halogen, $OJ_1$, $SJ_1$, $NJ_1J_2$, $N_3$, CN, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, C(=O)$OJ_1$, C(=O)$NJ_1J_2$, C(=O)$J_1$, O—C(=O)$NJ_1J_2$, N(H)C(=O)$NJ_1J_2$ and N(H)C(=S)$NJ_1J_2$;

each $J_1$ and $J_2$ is, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ aminoalkyl, substituted $C_1$-$C_6$ aminoalkyl or a protecting group; and $R_2$ and $R_3$ are each independently hydrogen or a hydroxyl protecting group.

In one embodiment, Q is an optionally substituted purine radical selected from adenine, guanine, hypoxanthine, xanthine, theobromine and caffeine.

In one embodiment, $R_1$ is selected from $(CH_2)_{1-2}CH_3$, $(CH_2)_{1-2}CH=CH_2$, $((CH_2)_{1-3}O(CH_2)_{1-3})_{1-3}H$, $(CH_2)_{1-3}S(CH_2)_{1-3}H$, $(CH_2)_2ON(CH_3)_2$, $(CH_2)_2O(CH_2)_2N(CH_3)_2$, $CH_2C(=O)N(-CH_3)_2$ and $CH_2C(=O)N(H)CH_3$. In a further embodiment, $R_1$ is selected from $CH_3$, $CH_2CH=CH_2$, $(CH_2)_2OCH_3$, $(CH_2)_2SCH_3$, $(CH_2)_2ON(CH_3)_2$, $CH_2C(=O)N(CH_3)_2$ and $CH_2C(=O)N(H)CH_3$.

In one embodiment, the alkoxy radical is $R_1O$.

In one embodiment, each hydroxyl protecting group is, independently, acetyl, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, benzoyl, p-phenylbenzoyl, 2,6-dichlorobenzyl, diphenylmethyl, p-nitrobenzyl, triphenylmethyl (trityl), 4-methoxytrityl, 4,4'-dimethoxytrityl, trimethylsilyl, triethylsilyl, t-butyldimethylsilyl, t-butyldiphenylsilyl, triphenylsilyl, triisopropylsilyl, benzoylformate, chloroacetyl, trichloroacetyl, trifluoroacetyl, pivaloyl, 9-fluorenyl-methyl carbonate, mesylate, tosylate, triflate, trityl, monomethoxytrityl, dimethoxytrityl, trimethoxytrityl or substituted pixyl. In further embodiment, each hydroxyl protecting group is, independently, acetyl, benzyl, benzoyl, 2,6-dichlorobenzyl, t-butyldimethylsilyl, t-butyl-diphenylsilyl, mesylate, tosylate, dimethoxytrityl (DMT), 9-phenylxanthine-9-yl (Pixyl) or 9-(p-methoxyphenyl)xanthine-9-yl (MOX). In yet further embodiment, each hydroxyl protecting group is, independently, acetyl, benzyl, t-butyldimethylsilyl, t-butyldiphenylsilyl or dimethoxytrityl. In yet further embodiment, each hydroxyl protecting group is, independently, trityl, monomethoxytrityl, dimethoxytrityl, trimethoxytrityl or a silyl group.

In one embodiment, the process of the present invention further comprises the step of reducing the 8-SH or 8-OH group of the 2'-O-substituted purine nucleoside.

In one embodiment, the reducing step includes desulfurization with a metal catalyst.

In one embodiment, the metal catalyst is Raney nickel, platinum, palladium on carbon (Pd/C), $Ni_2B$ or $NiCl_2$/$NaBH_4$.

In one embodiment, the reagent comprises a Lewis acid ester.

In one embodiment, the Lewis acid ester is a borane alkoxide or a magnesium alkoxide.

In one embodiment, the borane alkoxide is a trialkyl borate.

In one embodiment, the formula of the trialkyl borate is $B(OR_1)_3$, wherein $R_1$ is $(CH_2)_{0-2}CH_3$, $(CH_2)_{1-2}CH=CH_2$, $((CH_2)_{1-3}O(CH_2)_{1-3})_{1-3}H$, $(CH_2)_{1-3}S(CH_2)_{1-3}H$, $(CH_2)_2ON(CH_3)_2$, $(CH_2)_2O(CH_2)_2N(CH_3)_2$, $CH_2C(=O)N(CH_3)_2$ or $CH_2C(=O)N(H)CH_3$.

In one embodiment, the reagent is magnesium alkoxide of formula $MgO(R_1)_2$, wherein $R_1$ is $(CH_2)_{0-2}CH_3$, $(CH_2)_{1-2}CH=CH_2$, $((CH_2)_{1-3}O(CH_2)_{1-3})_{1-3}H$, $(CH_2)_{1-3}S(CH_2)_{1-3}H$, $(CH_2)_2ON(CH_3)_2$, $(CH_2)_2O(CH_2)_2N(CH_3)_2$, $CH_2C(=O)N(CH_3)_2$ or $CH_2C(=O)N(H)CH_3$.

In one embodiment, the reagent further includes a weak base selected from sodium bicarbonate, sodium carbonate, potassium bicarbonate or potassium carbonate.

In one embodiment, the organic phase is an alcohol, tetrahydrofuran, dimethylformamide, 1-methyl-2-pyrrolidone, dimethylacetamide, acetonitrile, dimethyl sulfoxide, dioxane, a chlorinated solvent or a mixture thereof.

In one embodiment, the organic phase is an alcohol. In one embodiment, the treating step includes heating at from about 120° C. to about 200° C. In one embodiment, the treating step is performed in a pressure sealed vessel.

In one embodiment, the 8,2'-cyclopurine nucleoside is selected from one of formulas II, III and IV:

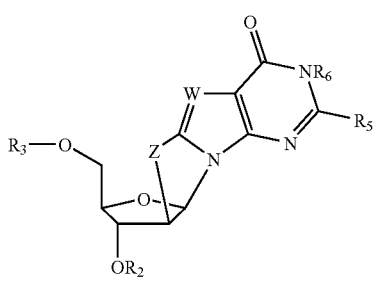

II

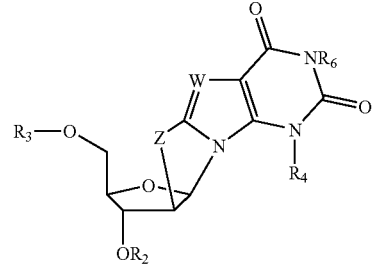

III

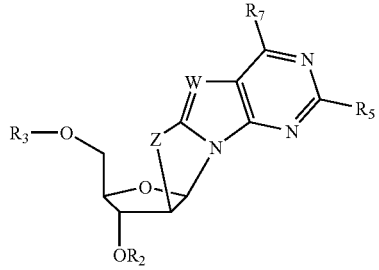

IV wherein:

$R_2$ and $R_3$ are each independently hydrogen or a hydroxyl protecting group;

W is N or $CR_8$;

$R_8$ is hydrogen or an optionally substituted group selected from amino, lower alkyl or lower alkoxy;

Z is S or O;

$R_4$ and $R_6$ are each independently selected from hydrogen, or an optionally substituted group selected from lower alkyl or lower alkoxy; and $R_5$ and $R_7$ are each independently hydrogen or an optionally substituted group selected from amino, lower alkyl or lower alkoxy.

In one embodiment, Z is S. In one embodiment, the 8,2'-cyclopurine nucleoside has formula II, $R_5$ is amino and $R_6$ is hydrogen.

In one embodiment, the present invention provides processes for the synthesis of a 2'-O-substituted purine nucleoside of formula V:

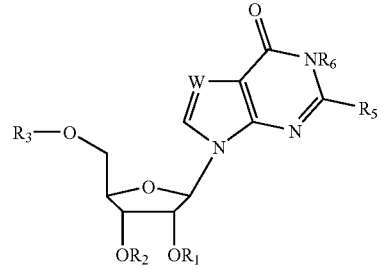

V wherein:

$R_1$ is $(CH_2)_{0-2}CH_3$, $(CH_2)_{1-2}CH=CH_2$, $((CH_2)_{1-3}O(CH_2)_{1-3})_{1-3}H$, $(CH_2)_{1-3}S(CH_2)_{1-3}H$, $(CH_2)_2ON(CH_3)_2$, $(CH_2)_2O(CH_2)_2N(CH_3)_2$, $CH_2C(=O)N(CH_3)_2$ or $CH_2C(=O)N(H)CH_3$;

$R_2$ and $R_3$ are each independently hydrogen or a hydroxyl protecting group;

W is N or $CR_8$;

$R_8$ is hydrogen or an optionally substituted group selected from lower alkyl and lower alkoxy;

$R_5$ is hydrogen or an optionally substituted group selected from amino, lower alkyl and lower alkoxy; and $R_6$ is hydrogen or an optionally substituted group selected from lower alkyl and lower alkoxy;

comprising the steps of:

a) providing a 8,2'-thioanhydro purine nucleoside of formula VI:

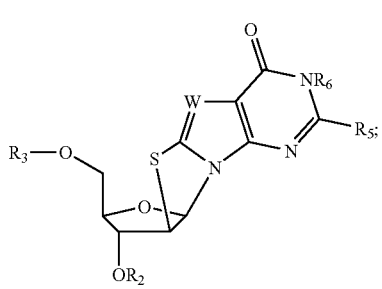

VI b) treating the 8,2'-thioanhydro purine nucleoside of formula VI with a Lewis acid ester and a weak base in an organic phase to yield a 2'-O-substituted 8-thiopurine nucleoside of formula VII:

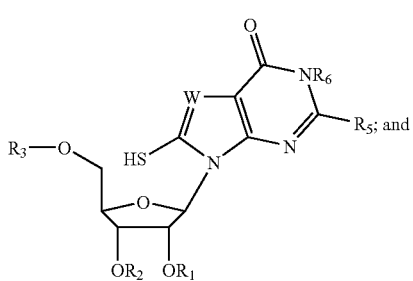

VII c) reducing the 2'-O-substituted 8-thiopurine nucleoside of formula (VII) to yield the 2'-O-substituted purine nucleoside of formula (V).

In one embodiment, of the invention, the processes further comprises the step of adding triphenylphosphorane or iodine.

In one embodiment, Q is an optionally substituted purine selected from adenine, guanine, hypoxanthine, xanthine, theobromine and caffeine.

In one embodiment, W is N; $R_1$ is $(CH_2)_2OCH_3$; $R_2$ and $R_3$ both are hydrogen; $R_5$ is amino; and $R_6$ is hydrogen. In one embodiment, the weak base is sodium bicarbonate, sodium carbonate, potassium bicarbonate or potassium carbonate. In one embodiment, the treating step includes heating at from about 120° C. to about 200° C. In one embodiment, the treating step is performed in a pressure sealed vessel.

In one embodiment, the Lewis acid ester is a borane or magnesium alkoxide. In one embodiment, the borane alkoxide is a trialkyl borate. In one embodiment, the formula of the trialkyl borate is $B(OR_1)_3$, wherein $R_1$ is selected from $(CH_2)_{0-2}CH_3$, $(CH_2)_{1-2}CH=CH_2$, $((CH_2)_{1-3}O(CH_2)_{1-3})_{1-3}H$, $(CH_2)_{1-3}S(CH_2)_{1-3}H$, $CH_2C(H)CH_2$, $(CH_2)_2ON(CH_3)_2$, $(CH_2)_2O(CH_2)_2N(CH_3)_2$, $CH_2C(=O)N(CH_3)_2$ and $CH_2C(=O)N(H)CH_3$. In one embodiment, the Lewis acid ester is magnesium alkoxide of formula $MgO(R_1)_2$, wherein $R_1$ is selected from $(CH_2)_{0-2}CH_3$, $(CH_2)_{1-2}CH=CH_2$, $((CH_2)_{1-3}O(CH_2)_{1-3})_{1-3}H$, $(CH_2)_{1-3}S(CH_2)_{1-3}H$, $CH_2C(H)CH_2$, $(CH_2)_2 ON(CH_3)_2$, $(CH_2)_2O(CH_2)_2N(CH_3)_2$, $CH_2C(=O)N(CH_3)_2$ and $CH_2C(=O)N(H)CH_3$.

In one embodiment, the reducing step includes desulfurization with a metal catalyst to obtain the 2'-O-substituted purine nucleoside of formula (I). In one embodiment, the metal catalyst is selected from Raney nickel, platinum, palladium on carbon (Pd/C), $Ni_2B$, and $NiCl_{2},NaBH_4$.

The present invention introduces an improved method that is expected to be a more efficient and inexpensive method to synthesize 2'-O-substituted purine nucleosides. In one aspect of the present invention, 2'-O-substituted purine nucleosides are prepared by ring opening of 8,2'-cyclopurine nucleosides using 3'-OH assisted borane-chelated alkyl groups, followed by reduction to afford a 2'-O-substituted purine nucleosides. The process described herein does not involve the formation of 2,6-diaminopurine riboside and their derivatives as required by current methods of synthesizing 2'-O-substituted purine nucleosides; therefore, the use of the expensive adenosine deaminase enzyme is not required to convert the alkylated 2,6-diaminopurine ribosides back to the original purine nucleoside derivatives. In addition, the process of the preparation of 2'-O-substituted purines in the present invention eliminates the step of the alkylation using alkyl bromides, thus eliminating the formation of the undesired 3'-O-alkyl-2,6-diaminopurine ribosides, and 2'-O-3'-O-dialkyl-2,6-diaminopurine ribosides. As such the process of the present invention is expected to provide the desired 2'-O-substituted purine nucleosides with much less impurities as compared to processes currently in use.

The present process is amenable to both small and large scale synthesis of 2'-O-substituted purine nucleosides. The process of the present invention will provide significant economic benefits in the production of 2'-O-substituted purines, including but not limited to 2'-O-methoxyethyl adenosine, 2'-O-methoxyethyl guanosine, 2'-O-methyl adenosine, 2'-O-methyl guanosine, and numerous other related 2'-O-substituted purine nucleosides.

DETAILED DESCRIPTION OF THE INVENTION

The present invention provides methods of preparing 2'-O-substituted purine nucleosides via an anhydro (or thioanhydro) ring opening of selected 8,2'-cyclopurine nucleosides. The 8,2'-cyclopurine nucleosides amenable to the present invention include a sulfur or oxygen atom that is bound to both the 2'-position of the sugar and to the 8 position of the purine base.

In certain preferred embodiments of the present invention, the 8,2'-cyclopurine nucleosides have one of formulas II, III, or IV:

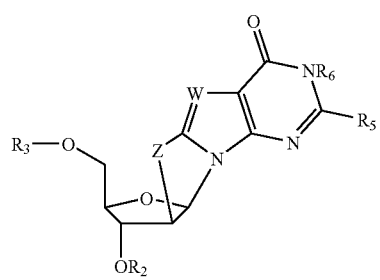

II

-continued

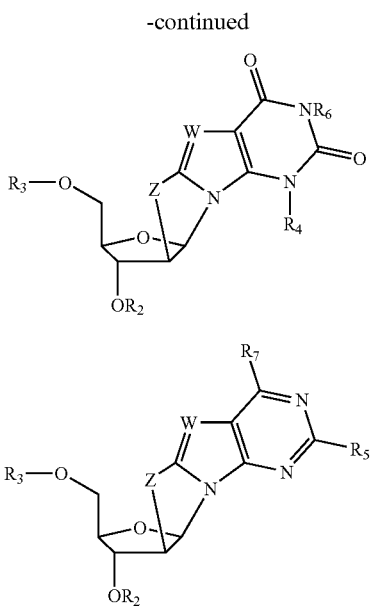

wherein:

$R_2$ and $R_3$ are each independently hydrogen or a hydroxyl protecting group;

W is N or $CR_8$;

$R_8$ is hydrogen or an optionally substituted group selected from amino, lower alkyl or lower alkoxy;

Z is S or O;

$R_4$ and $R_6$ are each independently selected from hydrogen, or an optionally substituted group selected from lower alkyl or lower alkoxy; and $R_5$ and $R_7$ are each independently hydrogen or an optionally substituted group selected from amino, lower alkyl or lower alkoxy.

In preferred embodiments, the 8,2'-cyclopurine nucleosides have formula II. In preferred embodiments, the present invention provides processes for the synthesis of 2'-O-substituted purine nucleosides of formula V. In further embodiments, the 2'-O-substituted purine nucleoside is 2'-methoxyethyl-8-mercapto guanosine having the formula:

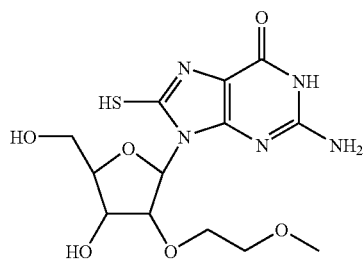

A Lewis acid ester is used in the ring opening step to convert the anhydro or thioanhydro 8,2'-cyclopurine nucleoside to the corresponding 2'-O-substituted purine nucleoside. The 8,2'-cyclopurine nucleoside is treated with a Lewis acid ester and a weak base (e.g. a trialkyl borate and magnesium alkoxide) followed by heating to provide the corresponding 2'-O-substituted purine nucleoside.

While not wishing to be bound by a specific theory, it is believed that the mechanism of ring opening of the anhydro or thioanhydro ring of a selected 8,2'-cyclopurine nucleoside involves nucleophilic attack at the 2'-carbon by a weak nucleophile. The nucleophilic attack is facilitated by the complexing of the Lewis acid ester to the bridging sulfur or oxygen. The resulting complex is believed to activate the 2'-carbon to nucleophilic attack by the weak nucleophile. An alternate theory is that the Lewis acid ester complexes to the 5' and 3' hydroxyl groups, causing a conformational change in the molecule, enabling attack by the weak nucleophile to give the desired product.

In one embodiment of the invention the Lewis acid ester used is a trialkyl borate. In certain embodiments, the trialkyl borate is $B(OR^1)_3$, wherein $R_1$ is $(CH_2)_{0-2}CH_3$, $(CH_2)_{1-2}CH=CH_2$, $((CH_2)_{1-3}O(CH_2)_{1-3})_{1-3}H$, $(CH_2)_{1-3}S(CH_2)_{1-3}H$, $(CH_2)_2ON(CH_3)_2$, $(CH_2)_2O(CH_2)_2N(CH_3)_2$, $CH_2C(=O)N(CH_3)_2$ or $CH_2C(=O)N(H)CH_3$. The trialkyl borate can be purchased or prepared such that the borate alkyl groups are identical to the alkyl groups of the nucleophile. For example, when 2'-O-methoxyethyl guanosine is being prepared, tris-(2-methoxylethyl) borate would preferably be the Lewis acid ester, and 2-methoxyethanol preferably would be the nucleophile. Tris-(2-methoxylethyl) borate is commercially available through Aldrich Chemical Company, Milwaukee, Wis. Alternatively, trialkyl borates can be prepared from borane and the alcohol that corresponds to the desired substituent for the 2'-position as illustrated above. Typically, borane, which is available as a 1.0 M solution in THF, is reacted with 3 equivalents of the respective alcohol. When the evolution of hydrogen is completed the solution is concentrated to remove the THF. The resulting solution, which contains the desired trialkyl borane in the desired alcohol, can be used in the instant process to achieve opening of the anhydro or thioanhydro ring as discussed above.

In another embodiment of the invention is the Lewis acid ester used is magnesium alkoxide of formula $MgO(R^1)_2$, wherein $R_1$ is $(CH_2)_{0-2}CH_3$, $(CH_2)_{1-2}CH=CH_2$, $((CH_2)_{1-3}O(CH_2)_{1-3})_{1-3}H$, $(CH_2)_{1-3}S(CH_2)_{1-3}H$, $(CH_2)_2ON(CH_3)_2$, $(CH_2)_2O(CH_2)_2N(CH_3)_2$, $CH_2C(=O)N(CH_3)_2$ or $CH_2C(=O)-N(H)CH_3$.

The term "Lewis acid ester," as used herein, has its usual meaning as a molecule or ion which can combine with another molecule or ion by forming a covalent bond with two electrons from the second molecule or ion. For use in the process of the invention, a Lewis acid ester is considered as an electron deficient species that can accept a pair of electrons. Particularly preferred are the di and tri valent hard acids. More particular are the divalent and trivalent cations of di and tri valent metals and their complexes including magnesium, calcium, aluminum, zinc, chromium, copper, boron, tin, mercury, iron, manganese, cadmium, gallium and barium. Their complex will include, but are not limited to, hydroxides, alkyls, alkoxides, di and trihalides particularly the trichlorides and trifluorides and organic acid ligands such as acetates. Especially preferred examples of Lewis acid esters useful in the instant process are borates, particularly alkyl borates.

The resulting 2'-O-substituted purine nucleosides are reduced with a metal catalyst to give 2'-O-substituted purine nucleosides. The anhydro or thioanhydro ring opening provides the predetermined 2'-O-substituent but also leaves a SH or OH group on the 8 position of the purine nucleoside. The reduction step will remove the SH or OH group. In certain embodiments of the present invention, the metal catalyst is selected from Raney nickel, platinum, palladium on carbon (Pd/C), $Ni_2B$, and $NiCl_2/NaBH_4$. Preferably, Raney nickel is used as a desulfurization agent in the process reducing of the 8,2'-thiocyclopurine nucleosides to the 2'-O-substituted purine nucleosides.

For the purposes of the present invention, purine nucleosides include naturally occurring purine bases such as adenine and guanine as well as non-naturally occurring purines such as hypoxanthine, xanthine, theobromine and caffeine. Many modified purines amenable to the present invention are known in the art (See for example *Chemistry of Nucleosides and Nucleotides, Volume* 1, Plenum Press, N.Y. 1988). The term purine nucleoside therefore contemplates all manner of purines and modified purines as well as optionally substituted and/or protected analogs thereof.

Nucleobases according to the invention include purines and pyrimidines such as adenine, guanine, cytosine, uridine, and thymine, as well as other synthetic and natural nucleobases such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, amino, thiol, thioalkyl, hydroxyl and other 8-substituted adenines and guanines, 5-trifluoromethyl and other 5-substituted uracils and cytosines, 7-methylguanine. Further purines and pyrimidines include those disclosed in U.S. Pat. No. 3,687, 808, those disclosed in the *Concise Encyclopedia Of Polymer Science And Engineering*, pages 858-859, Kroschwitz, J. I., ed. John Wiley & Sons, 1990, and those disclosed by English, et al., *Angewandte Chemie, International Edition* 1991, 30, 613.

8,2'-Cyclopurine nucleosides suitable for use in the processes of the invention include those that are unsubstituted as well as those having substitutions on the purine ring. A variety of such substituted purine substitutions are known in the art, for example, alkylation at the 5-position. See for example *Chemistry of Nucleosides and Nucleotides, Volume* 1 supra.

Purines bearing a variety of substitutions (i.e., purines bearing substituent groups) are known in the art. A representative list of such substituent groups amenable to the process of the present invention includes hydrocarbyl groups such as alkyl or substituted alkyl, alkenyl or substituted alkenyl, alkynyl or substituted alkynyl, carbocylo alkyl, carbocylo alkenyl, carbocylo aralkyl, aryl, aralkyl or substituted aralkyl. The substituent groups listed above can themselves bear substituent groups such as alkoxy, alcohol, benzyl, phenyl, nitro, thiol, thioalkoxy, halogen, or alkyl, aryl, alkenyl, or alkynyl groups, and ether groups.

In the process of the present invention, 8,2'-cyclopurine nucleosides are treated with an alcohol of formula $R_1$—OH. Representative $R_1$ groups include optionally substituted $C_1$-$C_{12}$ alkyl, optionally substituted $C_2$-$C_{12}$ alkenyl, optionally substituted $C_2$-$C_{12}$ alkynyl, amino, optionally substituted amino, optionally substituted amide, optionally substituted aralkyl, optionally substituted aralkyl, $CF_3$, CN, optionally substituted heterocycloalkyl, optionally substituted heterocycloalkaryl, optionally substituted aminoalkylamino, optionally substituted polyalkylamino and $((CH_2)_x—O(CH_2)_y)_mH$, wherein each x and each y are each independently selected from 1 to 5, m is 1 to 5; wherein each substituent group is, independently, halogen, optionally substituted $C_1$-$C_{12}$ alkyl, optionally substituted $C_2$-$C_{12}$ alkenyl, optionally substituted $C_2$-$C_{12}$ alkynyl, optionally substituted S—$C_1$-$C_{12}$ alkyl, (C(=O)—H), optionally substituted acyl, optionally substituted amino, optionally substituted amide, optionally substituted $C_1$-$C_{12}$ alkylamino, optionally substituted $C_1$-$C_{12}$ aminoalkoxy, optionally substituted $C_1$-$C_{12}$ alkylaminooxy, optionally substituted guanidinyl or a protecting group. Preferably, $R_1$ groups include $(CH_2)_{0-2}CH_3$, $(CH_2)_{1-2}CH=CH_2$, $((CH_2)_{1-3}O(CH_2)_{1-3})_{1-3}H$, $(CH_2)_{1-3}S(CH_2)_{1-3}H$, $CH_2C(H)CH_2$, $(CH_2)_2ON(CH_3)_2$, $(CH_2)_2O(CH_2)_2N(CH_3)_2$, $CH_2C(=O)—N(CH_3)_2$ and $CH_2C(=O)N(H)CH_3$.

A preferred list of $R_1$ groups includes without limitation, substituted or unsubstituted $C_1$-$C_{12}$ alkyl, substituted or unsubstituted $C_2$-$C_{12}$ alkenyl, or substituted or unsubstituted $C_2$-$C_{12}$ alkynyl wherein each substituted group independently comprises one or more substituent groups independently selected from halogen, $OJ_1$, $SJ_1$, $NJ_1J_2$, $N_3$, CN, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C(=O)OJ_1$, $C(=O)NJ_1J_2$, $C(=O)J_1$, O—$C(=O)NJ_1J_2$, $N(H)C(=O)NJ_1J_2$ and $N(H)C(=S)NJ_1J_2$; and each $J_1$ and $J_2$ is, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ aminoalkyl, substituted $C_1$-$C_6$ aminoalkyl or a protecting group. Another preferred list of $R_1$ groups includes without limitation, $(CH_2)_{1-2}CH_3$, $(CH_2)_{1-2}CH=CH_2$, $((CH_2)_{1-3}O(CH_2)_{1-3})_{1-3}H$, $(CH_2)_{1-3}S(CH_2)_{1-3}H$, $(CH_2)_2ON(CH_3)_2$, $(CH_2)_2O(CH_2)_2N—(CH_3)_2$, $CH_2C(=O)N(CH_3)_2$ and $CH_2C(=O)N(H)CH_3$. A further preferred list of $R_1$ groups includes without limitation, $CH_3$, $CH_2CH=CH_2$, $(CH_2)_2OCH_3$, $(CH_2)_2SCH_3$, $(CH_2)_2ON(CH_3)_2$, $CH_2C(=O)N—(CH_3)_2$ and $CH_2C(=O)N(H)CH_3$.

2'-O-Substituted purine nucleosides (substituted purine nucleosides) prepared according to the process of the present invention can be used to prepare a variety of compounds including oligonucleotides, oligonucleosides, mixed oligonucleotides/nucleosides, and related compounds known in the art.

In the context of this invention, the term "oligonucleotide" includes oligomers or polymers containing two or more nucleotide subunits. Nucleotides, as used herein, may include naturally occurring sugars, nucleobases, and intersugar (backbone) linkages as well as non-naturally occurring portions which function similarly. Such chemically modified or substituted oligonucleotides are often preferred over native forms because of properties such as, for example, enhanced cellular uptake and increased stability in the presence of nucleases.

Specific examples of some preferred oligonucleotides envisioned for this invention may contain, in addition to phosphodiester intersugar linkages (backbones), modified intersugar linkages such as phosphorothioates, phosphotriesters, methyl phosphonates, chain alkyl or cycloalkyl intersugar linkages or short chain heteroatomic or heterocyclic intersugar linkages.

As used herein, the term oligonucleoside includes oligomers or polymers containing two or more nucleoside subunits having a non-phosphorous linking moiety. Oligonucleosides according to the invention have a ribofuranose moieties attached to a nucleobases through glycosyl bonds. An oligonucleotide/nucleoside for the purposes of the present invention is a mixed backbone oligomer having at least two nucleosides covalently bound by a non-phosphate linkage and at least one phosphorous containing covalent bond with a nucleotide, and wherein at least one of the monomeric nucleotide or nucleoside units is a 2'-O-substituted compound prepared using the process of the present invention. An oligo-nucleotide/nucleoside can additionally have a plurality of nucleotides and nucleosides coupled through phosphorous containing and/or non-phosphorous containing linkages.

Methods of coupling 2'-O-substituted compounds prepared using the process of the present invention include conversion to the phosphoramidite followed by solution phase or solid phase chemistries. Representative solution phase techniques are described in U.S. Pat. No. 5,210,264, issued May 11, 1993 and commonly assigned with this invention. Representative solid phase techniques are those typically employed for DNA and RNA synthesis utilizing standard phosphoramidite chemistry. (see, e.g., Protocols For Oligonucleotides And Analogs, Agrawal, S., ed., Humana Press, Totowa, N.J., 1993.) A preferred synthetic solid phase synthesis utilizes phosphoramidites as activated phosphates. The phosphoramidites utilize $P^{III}$ chemistry. The intermediate phosphite compounds are subsequently oxidized to the $P^V$ state using known methods. This allows for synthesis of linkages including phosphodiester or phosphorothioate phosphate linkages depending upon oxidation conditions selected. Other phosphate linkages can also be generated. A representative list of suitable linkages includes phosphodiester, phosphotriester, hydrogen phosphonate, alkylphosphonate, alkylphosphonothioate, arylphosphonothioate, phosphorothioate, phosphorodithioate, phosphoramidate, ketone, sulfone, carbonate, thioamidate and other such moieties as are known in the art. Alkylphosphonothioate linkages are disclosed in WO 94/02499.

Standard methods and techniques used to increase the coupling efficiency of oligonucleotide synthesis include activation of 3' and or 5' functional groups. Some commonly activated groups are phosphate and phosphite which give the corresponding activated phosphate and activated phosphite (see e.g., *Nucleic Acids in Chemistry and Biology*; Blackburn, G. M., Gait M. J., Eds. Chemical Synthesis; IL: New York, 1990, Chapter 3, p. 98). Many others are known and can be used herein.

The term "alkyl," as used herein, refers to a saturated straight or branched hydrocarbon radical containing up to twenty four carbon atoms. Alkyl groups include but are not limited to substituted and unsubstituted straight chain, branch chain, and alicyclic hydrocarbons, including methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl and other higher carbon alkyl groups. Further examples include 2-methylpropyl, 2-methyl-4-ethylbutyl, 2,4-diethylpropyl, 3-propylbutyl, 2,8-dibutyldecyl, 6,6-dimethyloctyl, 6-propyl-6-butyloctyl, 2-methylbutyl, 2-methylpentyl, 3-methylpentyl, 2-ethylhexyl and other branched chain groups.

The term "alkenyl," as used herein, refers to a straight or branched hydrocarbon chain radical containing up to twenty four carbon atoms and having at least one carbon-carbon double bond. Examples of alkenyl groups include, but are not limited to, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substitutent groups.

The term "alkoxy" refers to an alkyl ether radical, wherein the term alkyl is as defined herein.

The term "alkynyl," as used herein, refers to a straight or branched hydrocarbon radical containing up to twenty four carbon atoms and having at least one carbon-carbon triple bond. Examples of alkynyl groups include, but are not limited to, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substitutent groups. The term "aminoalkyl" as used herein, refers to an amino substituted alkyl radical. This term is meant to include $C_1$-$C_{12}$ alkyl groups having an amino substituent at any position and wherein the alkyl group attaches the aminoalkyl group to the parent molecule. The alkyl and/or amino portions of the aminoalkyl group can be further substituted with substituent groups.

An "amide" is a chemical moiety with formula —(R)$_i$—C(O)NHR' or —(R)$_i$—NHC(O)R', where R and R' are independently selected from the group consisting of alkyl, cycloalkyl, aryl, heteroaryl (bonded through a ring carbon) and heteroalicyclic (bonded through a ring carbon), and where i is 0 or 1. An amide may be an amino acid or a peptide molecule attached to a molecule of the present invention, thereby forming a prodrug. The term R or the term R', appearing by itself and without a number designation, unless otherwise defined, refers to an optionally substituted moiety selected from the group consisting of alkyl, cycloalkyl, heteroalkyl, aryl, heteroaryl and heterocycloalkyl. Such R and R' groups should be understood to be optionally substituted as defined herein. Whether an R group has a number designation or not, every R group, including R, R' and $R_j$ where j=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence.

The terms "aralkyl" and "arylalkyl," as used herein, refer to a radical formed between an alkyl group and an aryl group wherein the alkyl group is used to attach the aralkyl group to a parent molecule. Examples include, but are not limited to, benzyl, phenethyl and the like. Aralkyl groups as used herein may optionally include further substitutent groups attached to the alkyl, the aryl or both groups that form the radical group.

The term "aryl" is intended to denote monocyclic and polycyclic aromatic groups including, for example, phenyl, naphthyl, xylyl, pyrrole, and furyl groups. Although aryl groups (e.g., imidazo groups) can include as few as 3 carbon atoms, preferred aryl groups have 6 to about 14 carbon atoms, more preferably 6 to about 10 carbon atoms.

The term "aralkyl" is intended to denote groups containing both alkyl and aryl portions wherein the point of attachment of such groups is through an alkyl portion thereof. Benzyl groups provide one example of an aralkyl group.

The term "desulfurization" as used herein refers to the removal of the thio group from the purine ring.

The term "halo" or, alternatively, "halogen" means fluoro, chloro, bromo or iodo. Preferred halo groups are fluoro, chloro and bromo.

The term "heterocycloalkyl" refers to a cycloalkyl radical as described, in which one or more or all carbon atoms of the saturated or unsaturated cyclic radical are replaced by a heteroatom from the group consisting of N, O, and S. Examples of heterocycloalkyls include piperazinyl, morpholinyl, tetrahydropyranyl, tetrahydrofuranyl, piperidinyl, pyrrolidinyl and the like.

A number of substituent groups can be introduced into compounds of the invention in a protected (blocked) form and subsequently de-protected to form a final, desired compound. Substituent groups include groups covalently attached to the purine ring and the $R^1$ group of the alcohol $R^1$—OH described above. In general, protecting groups render chemical functionality inert to specific reaction conditions and can be appended to and removed from such functionality in a molecule without substantially damaging the remainder of the molecule. See, e.g., Greene and Wuts, *Protective Groups in Organic Synthesis*, 2d ed, John Wiley & Sons, New York, 1991. For example, amino groups can be protected as phthalimido groups or as 9-fluorenylmethoxycarbonyl (FMOC) groups and carboxyl groups can be protected as fluorenylmethyl groups. Representative hydroxyl protecting groups are described by Beaucage, et al., *Tetrahedron* 1992, 48, 2223. Preferred hydroxyl protecting groups are acid-labile, such as the trityl, monomethoxytrityl, dimethoxytrityl, trimethoxytrityl and a silyl group. A silyl group is a silyl protecting group and includes a conventional silyl protecting group, such as trialkylsilyl group, for example the trimethylsilyl group. Other silyl protecting groups include triarylsilyl groups, trialkoxysilyl groups and triaryloxysilyl groups.

In the process of the invention, the reagent, the weak base, and 8,2'-cyclopurine nucleosides are treated in a reaction vessel. The reaction vessel may be any container known in the art to be suitable for reactions wherein reactants are heated. Preferably, the reaction vessel is a pressure sealed vessel, and more preferably, a pressure sealed vessel. In preferred embodiments the reagent, the weak base, and 8,2'-cyclopurine nucleosides in an organic phase are treated by heating at from about 120° C. to about 200° C. In certain embodiments, the organic phase is a solvent selected from alcohol, tetrahydrofuran, dimethylformamide, 1-methyl-2-pyrrolidone, dimethylacetamide, acetonitrile, chlorinated solvent, dimethyl sulfoxide, dioxane, and mixtures thereof. Preferably, the solvent is an alcohol, for example, 2-methoxyethanol. In certain embodiments, the weak base is selected from the group consisting of sodium bicarbonate, sodium carbonate, potassium bicarbonate, and potassium carbonate.

Additional objects, advantages, and novel features of this invention will become apparent to those skilled in the art upon examination of the examples thereof provided below.

Example 1

8,2'-Anhydro-8-mercapto-9-b-D-arabinofuranosylguanine 8,2'-Anhydro-8-mercapto-9-b-D-arabinofuranosylguanine is prepared according to the reported procedure in Journal of Carbohydrate, Nucleoside, Nucleotides, 4(6), 409-413 (1977), or Journal of Heterocyclic chemistry, 1179-1180 (1973), or Canadian Journal of Chemistry, 50, 1100-1104, 1972, or Canadian Journal of Chemistry, 50, 2249-2249 (1972).

Example 2

2'-Methoxyethyl-8-mercapto guanosine 8,2'-Anhydro-8-mercapto-9-b-D-arabinofuranosylguanine (1 mmole), tris(2-methoxyethyl)borate (3.5 mmole), sodium bicarbonate (catalyst), anhydrous 2-methoxyethanol (100 mL), and dimethylformamide or any other polar solvent (200 mL) are mixed and heated in a bomb to 130-140° C. for 32 h. The solvent and other volatiles are removed and the residue is dissolved in water (500 mL) and heated to boiling for 1 h to hydrolyze borate esters. The water is removed under reduced pressure and the remaining residue is crystallized from hot methanol to yield 2'-methoxyethyl-8-mercapto guanosine.

Example 3

2'-Methoxyethyl-8-mercapto guanosine 8,2'Anhydro-8-mercapto-9-b-D-arabinofuranosylguanine (1 mmole), tris-methylborate (3.5 mmole), sodium bicarbonate (catalyst), anhydrous 2-methoxyethanol (100 mL), and dimethylformamide or any other polar solvent (200 mL) are mixed and heated in a bomb to 130-140° C. for 32 h. The solvent and other volatiles are removed. The residue is dissolved in water (500 mL) and heated to boiling for 1 h to hydrolyze borate esters. The water is removed under reduced pressure and the remaining residue is crystallized from hot methanol to yield 2'-methoxyethyl-8-mercapto guanosine.

Example 4

2'-Methoxyethyl-8-mercapto guanosine 8,2'-Anhydro-8-mercapto-9-b-D-arabinofuranosylguanine (1 mmole), tris-(2-N,N-dimethylaminoethyl)borate (3.5 mmole), sodium bicarbonate (catalyst), anhydrous 2-methoxyethanol (100 mL), and dimethylformamide or any other polar solvent (200 mL) are mixed and heated in a bomb to 130-140° C. for 32 h. The solvent and other volatiles are removed and the residue is dissolved in water (500 mL) and heated to boiling for 1 h to hydrolyze borate esters. The water is removed under reduced pressure and the remaining residue is crystallized from hot methanol to yield 2'-methoxyethyl-8-mercapto guanosine.

Example 5

2'-O-Methoxyethylguanosine

8-Thio-2'-O-methoxyethylguanosine (1 mmole) is dissolved in water and the solution is heated at reflux with Raney nickel for 6 h. The product is then isolated by passing the solution through a short pad of celite and is further crystallized to afford 2'-O-methoxyethylguanosine.

Example 6

2'-O-Methylguanosine

8-Thio-2'-O-methylguanosine (1 mmole) is dissolved in water and the solution is heated at reflux with Raney nickel for 6 h. The product is isolated by passing the solution through a short pad of celite and is further crystallizing to afford 2'-O-methylguanosine.

Example 7

2'-O-(2-N,N-Dimethylaminoethyl)guanosine

8-Thio-2'-O-(2-N,N-dimethylaminoethyl)guanosine (1 mmole) is dissolved in water and the solution is heated at reflux with Raney nickel for 10 h. The product is isolated by passing the solution through a short pad of celite and is further crystallized to afford 2'-O-(2-N,N-dimethylaminoethyl)guanosine.

Example 8

2'-O-Methoxyethylguanosine

8-Thio-2'-O-methoxyethylguanosine (1 mmole) is dissolved in water and the solution is heated at reflux with nickel boride for 16 h. The product is then isolated by passing the solution through a short pad of celite and is further crystallized to afford 2'-O-methoxyethylguanosine.

Example 9

2'-O-Methylguanosine

8-Thio-2'-O-methylguanosine (1 mmole) is dissolved in water and the solution is heated at reflux with nickel boride for 16 h. The product is isolated by passing the solution through a short pad of celite and is further crystallized to afford 2'-O-methylguanosine.

Example 10

2'-O-(2-N,N-Dimethylaminoethyl)guanosine

8-Thio-2'-O-(2-N,N-dimethylaminoethyl)guanosine (1 mmole) is dissolved in water and the solution is heated at reflux with nickel boride for 15 h. The product is isolated by passing the solution through a short pad of celite and is further crystallized to afford 2'-O-(2-N,N-dimethylaminoethyl)guanosine.

What is claimed is:

1. A process for the synthesis of a 2'-O-substituted purine nucleoside comprising the steps of:
   i) providing an 8,2'-cyclopurine nucleoside having an anhydro or thioanhydro linkage in an organic phase; and
   ii) treating said 8,2'-cyclopurine nucleoside with a reagent that provides an alkoxy radical capable of opening said anhydro linkage thereby providing said 2'-O-substituted purine nucleoside.

2. The process of claim 1 further comprising the step of adding triphenylphosphorane or iodine.

3. The process of claim 1 wherein said 2'-O-substituted purine nucleoside has formula I:

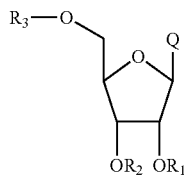

wherein:
Q is an optionally substituted purine;
$R_1$ is substituted or unsubstituted $C_1$-$C_{12}$ alkyl, substituted or unsubstituted $C_2$-$C_{12}$ alkenyl, or substituted or unsubstituted $C_2$-$C_{12}$ alkynyl;
wherein each substituted group independently comprises one or more substituent groups independently selected from halogen, $OJ_1$, $SJ_1$, $NJ_1J_2$, $N_3$, CN, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, C(=O)$OJ_1$, C(=O)$NJ_1J_2$, C(=O)$J_1$, O—C(=O)$NJ_1J_2$, N(H)C(=O)$NJ_1J_2$ and N(H)C(=S)$NJ_1J_2$;
each $J_1$ and $J_2$ is, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ aminoalkyl, substituted $C_1$-$C_6$ aminoalkyl or a protecting group; and
$R_2$ and $R_3$ are each independently hydrogen or a hydroxyl protecting group.

4. The process of claim 3 wherein Q is an optionally substituted purine radical selected from adenine, guanine, hypoxanthine, xanthine, theobromine and caffeine.

5. The process of claim 3 wherein $R_1$ is selected from $(CH_2)_{1-2}CH_3$, $(CH_2)_{1-2}CH=CH_2$, $((CH_2)_{1-3}O(CH_2)_{1-3})_{1-3}H$, $(CH_2)_{1-3}S(CH_2)_{1-3}H$, $(CH_2)_2ON(CH_3)_2$, $(CH_2)_2O(CH_2)_2N(CH_3)_2$, $CH_2C(=O)N(—CH_3)_2$ and $CH_2C(=O)N(H)CH_3$.

6. The process of claim 5 wherein $R_1$ is selected from $CH_3$, $CH_2CH=CH_2$, $(CH_2)_2OCH_3$, $(CH_2)_2SCH_3$, $(CH_2)_2ON(CH_3)_2$, $CH_2C(=O)N(CH_3)_2$ and $CH_2C(=O)N(H)CH_3$.

7. The process of claim 1 wherein the alkoxy radical is $R_1O$.

8. The process of claim 3 wherein each hydroxyl protecting group is, independently, acetyl, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, benzoyl, p-phenylbenzoyl, 2,6-dichlorobenzyl, diphenylmethyl, p-nitrobenzyl, triphenylmethyl (trityl), 4-methoxytrityl, 4,4'-dimethoxytrityl, trimethylsilyl, triethylsilyl, t-butyldimethylsilyl, t-butyldiphenylsilyl, triphenylsilyl, triisopropylsilyl, benzoylformate, chloroacetyl, trichloroacetyl, trifluoroacetyl, pivaloyl, 9-fluorenyl-methyl carbonate, mesylate, tosylate, triflate, trityl, monomethoxytrityl, dimethoxytrityl, trimethoxytrityl or substituted pixel.

9. The process of claim 3 wherein each hydroxyl protecting group is, independently, acetyl, benzyl, benzoyl, 2,6-dichlorobenzyl, t-butyldimethylsilyl, t-butyldiphenylsilyl, mesylate, tosylate, dimethoxytrityl (DMT), 9-phenylxanthine-9-yl (Pixyl) or 9-(p-methoxyphenyl)xanthine-9-yl (MOX).

10. The process of claim 3 wherein each hydroxyl protecting group is, independently, acetyl, benzyl, t-butyldimethylsilyl, t-butyldiphenylsilyl or dimethoxytrityl.

11. The process of claim 3 wherein each hydroxyl protecting group is, independently, trityl, monomethoxytrityl, dimethoxytrityl, trimethoxytrityl or a silyl group.

12. The process of claim 3 further comprising the step of reducing the 8-SH or 8-OH group of the 2'-O-substituted purine nucleoside.

13. The process of claim 12 wherein the reducing step includes desulfurization with a metal catalyst.

14. The process of claim 13 wherein the metal catalyst is Raney nickel, platinum, palladium on carbon (Pd/C), $Ni_2B$ or $NiCl_2/NaBH_4$.

15. The process of claim 1 wherein the reagent comprises a Lewis acid ester.

16. The process of claim 15 wherein the Lewis acid ester is a borane alkoxide or a magnesium alkoxide.

17. The process of claim 16 wherein the borane alkoxide is a trialkyl borate.

18. The process of claim 17 wherein the formula of the trialkyl borate is $B(OR_1)_3$, wherein $R_1$ is $(CH_2)_{0-2}CH_3$, $(CH_2)_{1-2}CH=CH_2$, $((CH_2)_{1-3}O(CH_2)_{1-3})_{1-3}H$, $(CH_2)_{1-3}S(CH_2)_{1-3}H$, $(CH_2)_2ON(CH_3)_2$, $(CH_2)_2O(CH_2)_2N(CH_3)_2$, $CH_2C(=O)N(CH_3)_2$ or $CH_2C(=O)N(H)CH_3$.

19. The process of claim 1 wherein the reagent is magnesium alkoxide of formula $MgO(R_1)_2$, wherein $R_1$ is $(CH_2)_{0-2}CH_3$, $(CH_2)_{1-2}CH=CH_2$, $((CH_2)_{1-3}O(CH_2)_{1-3})_{1-3}H$, $(CH_2)_{1-3}S(CH_2)_{1-3}H$, $(CH_2)_2ON(CH_3)_2$, $(CH_2)_2O(CH_2)_2N(CH_3)_2$, $CH_2C(=O)N(CH_3)_2$ or $CH_2C(=O)N(H)CH_3$.

20. The process of claim 1 wherein the reagent further includes a weak base selected from sodium bicarbonate, sodium carbonate, potassium bicarbonate or potassium carbonate.

21. The process of claim 1 wherein the organic phase is an alcohol, tetrahydrofuran, dimethylformamide, 1-methyl-2-pyrrolidone, dimethylacetamide, acetonitrile, dimethyl sulfoxide, dioxane, a chlorinated solvent or a mixture thereof.

22. The process of claim 21 wherein the organic phase is an alcohol.

23. The process of claim 1 wherein the treating step includes heating at from about 120° C. to about 200° C.

24. The process of claim 1 wherein the treating step is performed in a pressure sealed vessel.

25. The process of claim 1 wherein the 8,2'-cyclopurine nucleoside is selected from one of formulas II, III and IV:

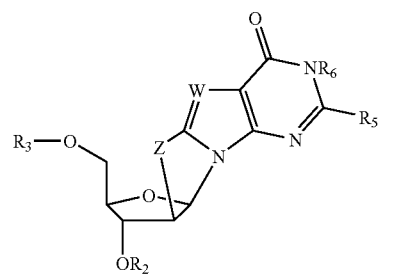

II

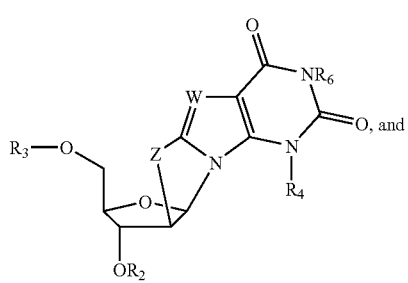

III

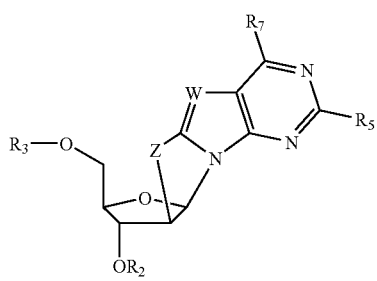

IV wherein:
$R_2$ and $R_3$ are each independently hydrogen or a hydroxyl protecting group;
W is N or $CR_8$;
$R_8$ is hydrogen or an optionally substituted group selected from amino, lower alkyl or lower alkoxy;
Z is S or O;
$R_4$ and $R_6$ are each independently selected from hydrogen, or an optionally substituted group selected from lower alkyl or lower alkoxy; and
$R_5$ and $R_7$ are each independently hydrogen or an optionally substituted group selected from amino, lower alkyl or lower alkoxy.

26. The process of claim 25 wherein Z is S.

27. The process of claim 26 wherein the 8,2'-cyclopurine nucleoside has formula II, $R_5$ is amino and $R_6$ is hydrogen.

28. A process for the synthesis of a 2'-O-substituted purine nucleoside of formula V:

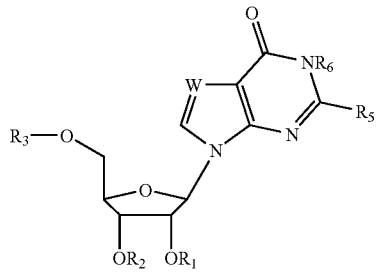

V wherein:
$R_1$ is $(CH_2)_{0-2}CH_3$, $(CH_2)_{1-2}CH=CH_2$, $((CH_2)_{1-3}O(CH_2)_{1-3})_{1-3}H$, $(CH_2)_{1-3}S(CH_2)_{1-3}H$, $(CH_2)_2ON(CH_3)_2$, $(CH_2)_2O(CH_2)_2N(CH_3)_2$, $CH_2C(=O)N(CH_3)_2$ or $CH_2C(=O)N(H)CH_3$;
$R_2$ and $R_3$ are each independently hydrogen or a hydroxyl protecting group;
W is N or $CR_8$;
$R_8$ is hydrogen or an optionally substituted group selected from lower alkyl and lower alkoxy;
$R_5$ is hydrogen or an optionally substituted group selected from amino, lower alkyl and lower alkoxy; and
$R_6$ is hydrogen or an optionally substituted group selected from lower alkyl and lower alkoxy;
comprising the steps of:
a) providing a 8,2'-thioanhydro purine nucleoside of formula VI:

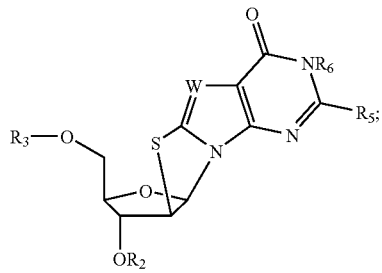

VI b) treating the 8,2'-thioanhydro purine nucleoside of formula VI with a Lewis acid ester and a weak base in an organic phase to yield a 2'-O-substituted 8-thiopurine nucleoside of formula VII:

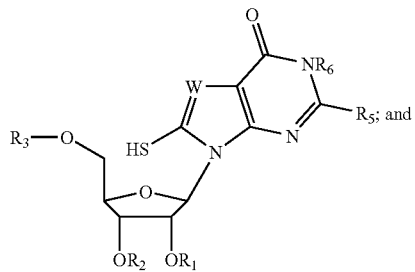

VII c) reducing the 2'-O-substituted 8-thiopurine nucleoside of formula (VII) to yield the 2'-O-substituted purine nucleoside of formula (V).

29. The process of claim 28 further comprising the step of adding triphenylphosphorane or iodine.

30. The process of claim 28 wherein Q is an optionally substituted purine selected from adenine, guanine, hypoxanthine, xanthine, theobromine and caffeine.

31. The process of claim 30 wherein:
W is N;
$R_1$ is $(CH_2)_2OCH_3$;
$R_2$ and $R_3$ are each hydrogen;
$R_5$ is amino; and
$R_6$ is hydrogen.

32. The process of claim 28 wherein the weak base is sodium bicarbonate, sodium carbonate, potassium bicarbonate or potassium carbonate.

33. The process of claim 28 wherein the treating step includes heating at from about 120° C. to about 200° C.

34. The process of claim 28 wherein the treating step is performed in a pressure sealed vessel.

35. The process of claim 28 wherein the Lewis acid ester is a borane or magnesium alkoxide.

36. The process of claim 35 wherein the borane alkoxide is a trialkyl borate.

37. The process of claim 36 wherein the formula of the trialkyl borate is $B(OR_1)_3$, wherein $R_1$ is selected from $(CH_2)_{0-2}CH_3$, $(CH_2)_{1-2}CH=CH_2$, $((CH_2)_{1-3}O(CH_2)_{1-3})_{1-3}H$, $(CH_2)_{1-3}S(CH_2)_{1-3}H$, $CH_2C(H)CH_2$, $(CH_2)_2ON(CH_3)_2$, $(CH_2)_2O(CH_2)_2N(CH_3)_2$, $CH_2C(=O)N(CH_3)_2$ and $CH_2C(=O)N(H)-CH_3$.

38. The process of claim 28 wherein the Lewis acid ester is magnesium alkoxide of formula $MgO(R_1)_2$, wherein $R_1$ is selected from $(CH_2)_{0-2}CH_3$, $(CH_2)_{1-2}CH=CH_2$, $((CH_2)_{1-3}O(CH_2)_{1-3})_{1-3}H$, $(CH_2)_{1-3}S(CH_2)_{1-3}H$, $CH_2C(H)CH_2$, $(CH_2)_2ON(CH_3)_2$, $(CH_2)_2O(CH_2)_2N(CH_3)_2$, $CH_2C(=O)N(CH_3)_2$ and $CH_2C(=O)N(H)CH_3$.

39. The process of claim 28 wherein the reducing step includes desulfurization with a metal catalyst to obtain the 2'-O-substituted purine nucleoside of formula (II).

40. The process of claim 28 wherein the metal catalyst is selected from Raney nickel, platinum, palladium on carbon (Pd/C), $Ni_2B$, and $NiCl_2/NaBH_4$.

* * * * *